US011785937B2

(12) United States Patent
De Larichaudy et al.

(10) Patent No.: US 11,785,937 B2
(45) Date of Patent: Oct. 17, 2023

(54) METHOD FOR THE CRYOPRESERVATION OF CELLS FOR THERAPEUTIC PURPOSES

(71) Applicant: LABORATOIRE FRANCAIS DU FRACTIONNEMENT ET DES BIOTECHNOLOGIES, Les Ulis (FR)

(72) Inventors: Joffrey De Larichaudy, Malakoff (FR); Sandy Cazalon Nemorin, Longjumeau (FR)

(73) Assignee: Laboratoire Francais du Fractionnement et des Biotechnologies, Puteaux (FR)

( * ) Notice: Subject to any disclaimer, the term of this patent is extended or adjusted under 35 U.S.C. 154(b) by 289 days.

(21) Appl. No.: 16/766,900

(22) PCT Filed: Nov. 27, 2018

(86) PCT No.: PCT/FR2018/053012
§ 371 (c)(1),
(2) Date: May 26, 2020

(87) PCT Pub. No.: WO2019/102172
PCT Pub. Date: May 31, 2019

(65) Prior Publication Data
US 2021/0244016 A1 Aug. 12, 2021

(30) Foreign Application Priority Data
Nov. 27, 2017 (FR) ...................................... 1761213

(51) Int. Cl.
*A01N 1/02* (2006.01)
*A61K 47/18* (2017.01)
*A61K 47/20* (2006.01)

(52) U.S. Cl.
CPC .......... *A01N 1/0221* (2013.01); *A61K 47/183* (2013.01); *A61K 47/20* (2013.01)

(58) Field of Classification Search
CPC .................................................. A01N 1/0221
USPC ........................................................ 435/1.3
See application file for complete search history.

(56) References Cited

U.S. PATENT DOCUMENTS

2004/0043008 A1  3/2004  Vilquin et al.

FOREIGN PATENT DOCUMENTS

| EP | 0394788 A1 | 10/1990 |
| FR | 2810045 B1 | 9/2004 |
| WO | 2001093676 A1 | 12/2001 |
| WO | 2008061148 A3 | 10/2008 |
| WO | 2015066631 A9 | 7/2015 |
| WO | 2017001782 A1 | 1/2017 |
| WO | 2017001783 A1 | 1/2017 |

OTHER PUBLICATIONS

Schallmoser et al., Transfusion (2007) vol. 47, pp. 1436-1446.*
Dulbecco, "Dulbecco's Modified Eagle Medium/Nutrient Mixture F-12 Ham (DMEM/F12, 1:1 Mixture)," Product information, retrieved from the Internet: http://himedialabs.com/TD/AL187A.pdf, Jan. 2011.
International Search Report and Written Opinion issued in application No. PCT/FR2018/053012 dated Feb. 2, 2019.
Sensebe et al., "Good Manufacturing Practices Production of Mesenchymal Stem/Stromal Cells," Human Gene Therapy, vol. 22, pp. 19-26, Jan. 2011.

* cited by examiner

*Primary Examiner* — Taofiq A Solola
(74) *Attorney, Agent, or Firm* — Rouget F. Henschel; Potomac Law Group, PLLC

(57) ABSTRACT

The present invention relates to a composition comprising, in a physiologically acceptable medium:
  a) at least one saccharide,
  b) at least one amino acid,
  c) DMSO or at least one C3-C5 alkanediol,
  d) at least one antioxidant, and
  e) cells for therapeutic purposes,
said composition having a pH between 7.0 and 8.5, preferably between 7.0 and 8.3. It also relates to a method for the cryopreservation of at least one sample of cells for therapeutic purposes, comprising the following steps:
i) mixing the sample of cells for therapeutic purposes with ingredients a) to d) above and a physiologically acceptable medium, so as to obtain a composition having a pH between 7.0 and 8.5, preferably between 7.0 and 8.3, then
ii) freezing the composition obtained in step i).

22 Claims, No Drawings

METHOD FOR THE CRYOPRESERVATION OF CELLS FOR THERAPEUTIC PURPOSES

The present invention relates to a composition comprising, in a physiologically acceptable medium:
- a) at least one saccharide,
- b) at least one amino acid,
- c) DMSO or at least one C3-C5 alkanediol,
- d) at least one antioxidant, and
- e) cells for therapeutic purposes, said composition having a pH between 7.0 and 8.5, preferably between 7.0 and 8.3.

The present invention also relates to a method for the cryopreservation of at least one sample of cells for therapeutic purposes, comprising the following steps:
- i) mixing the sample of cells for therapeutic purposes with:
  - a) at least one saccharide,
  - b) at least one amino acid,
  - c) DMSO or at least one C3-C5 alkanediol,
  - d) at least one antioxidant, and a physiologically acceptable medium, so as to obtain a composition having a pH between 7.0 and 8.5, preferably between 7.0 and 8.3, then
- ii) freezing the composition obtained in step i).

Cryopreservation is a process in which biological samples are stored at low temperatures. The cryopreservation of biological material is generally carried out by freezing said material, in a suitable storage device such as a tube or a glass or plastic ampoule (generally called a "straw" or freezing tube in the field of cryopreservation), said storage device being suitable for long-term storage at a low temperature.

However, cryopreservation poses a number of technical problems and constraints. In particular, cellular lesions can occur during thawing, resulting in apoptosis or bursting of the cells. In addition, the survival of the cryopreserved cells may depend on the conditions and techniques employed during freezing.

Controlling the cooling rate is important: cooling at a slow rate allows an ordered crystallization of freezable water outside the cells; the cells dehydrate, shrink, and the water exits the cell. Otherwise, intracellular ice formation leads to destruction of the membrane structures, which is lethal to the cell.

For most mammalian cells, which is the case for cell therapy products and drugs, it is also essential to use cryoprotectants to preserve cell integrity and functionality.

Currently, the manufacturing of cell therapy products on an industrial scale (European or worldwide) poses new problems, such as stability of the administered end product and variability related to the initial biological material.

In most cases, the end product is preserved:
- fresh in a liquid medium (albumin or saline) with a storage period limited to a few hours or days, or
- frozen in a simple formulation based on DMSO, which is unstable and inefficient in the long term. The significant amount of dead cells and of debris with potentially immunogenic effects, and the toxicity to the patient of commonly used excipients, are all limitations. Most of the time, washing the cells before administration in order to remove these toxic elements (biological or not) is indicated; these solutions are therefore not compatible with an industrial distribution. In addition, they offer little flexibility in administration and storage, unlike other "classic" drug classes.

There is therefore a need for the development of a cell therapy product and/or drug which is stable in the long term (i.e. for several months), is easy to use, directly injectable, and nontoxic.

Applications WO2017/001782 and WO2017/001783 describe cryopreservation compositions comprising human albumin and coenzyme Q10 or L-cysteine. However, such compositions are not optimal for the preservation of certain cell types.

There is therefore a need for the development of a cell therapy product and/or drug that is stable in the long term (i.e. for several months or even years), and in which cell viability and functionality are preserved.

The present invention makes it possible to meet this need. Indeed, the composition according to the invention makes it possible to obtain cell therapy products comprising cells for therapeutic purposes, ready for use (i.e. ready to be injected without washing, which eliminates any additional manipulations causing a decrease in viability and a loss of cells), stable in the long term after freezing and stable in the medium term after thawing (i.e. for one to several hours), easy to use, and non-toxic. In addition, the composition according to the invention makes it possible to preserve the viability of cells for therapeutic purposes, and their functionality is maintained.

The present invention thus relates to a composition comprising, in a physiologically acceptable medium:
- a) at least one saccharide,
- b) at least one amino acid,
- c) DMSO or at least one C3-C5 alkanediol,
- d) at least one antioxidant, and
- e) cells for therapeutic purposes, said composition having a pH between 7.0 and 8.5, preferably between 7.0 and 8.3. This composition is called "composition according to the invention" in the present application.

The present invention also relates to a method for the cryopreservation of at least one sample of cells for therapeutic purposes, comprising the following steps:
- i) mixing the sample of cells for therapeutic purposes with:
  - a) at least one saccharide,
  - b) at least one amino acid,
  - c) DMSO or at least one C3-C5 alkanediol,
  - d) at least one antioxidant, and
  - a physiologically acceptable medium, so as to obtain a composition having a pH between 7.0 and 8.5, preferably between 7.0 and 8.3, then
- ii) freezing the composition obtained in step i).

The present invention also relates to the use of a composition comprising, in a physiologically acceptable medium:
- a) at least one saccharide,
- b) at least one amino acid,
- c) DMSO or at least one C3-C5 alkanediol,
- d) at least one antioxidant, and having a pH between 7.0 and 8.5, preferably between 7.0 and 8.3, for the cryopreservation of at least one sample of cells for therapeutic purposes.

The composition according to the invention therefore comprises, in a physiologically acceptable medium:
- a) at least one saccharide,
- b) at least one amino acid,
- c) DMSO or at least one C3-C5 alkanediol,
- d) at least one antioxidant, and
- e) cells for therapeutic purposes.

In addition, the composition has a pH between 7.0 and 8.5, preferably between 7.0 and 8.3.

"Physiologically acceptable medium" is understood to mean an aqueous medium comprising at least one electrolyte. The electrolytes are, for example, salts of sodium, potassium, magnesium, and/or calcium with anions such as chloride, acetate, carbonate, hydrogencarbonate, hydroxide, or citrate. Preferably, the physiologically acceptable medium is an aqueous medium comprising at least sodium chloride, potassium chloride, and calcium chloride. Preferably, the physiologically acceptable medium further comprises sodium acetate and trisodium citrate.

Sodium is preferably present in the composition according to the invention in a concentration of between 130 and 200 mmol/L, preferably between 135 and 190 mmol/L, more preferably between 138 and 188 mmol/L.

Potassium is preferably present in the composition according to the invention in a concentration of between 0.5 and 5.0 mmol/L, preferably between 1.0 and 4.5 mmol/L, more preferably between 1.5 and 4.0 mmol/L.

Calcium is preferably present in the composition according to the invention in a concentration of between 0.01 and 10 mmol/L, preferably between 0.01 and 1 mmol/L, more preferably between 0.01 and 0.05 mmol/L.

Chloride is preferably present in the composition according to the invention in a concentration of between 40 and 110 mmol/L, preferably between 70 and 105 mmol/L, more preferably between 65 and 100 mmol/L.

Magnesium is preferably present in the composition according to the invention in a concentration of between 0 and 5 mmol/L, preferably between 0.5 and 4.5 mmol/L, more preferably between 1 and 3.5 mmol/L.

Preferably, the physiologically acceptable medium is such that the composition containing it has a pH between 7.0 and 8.5, preferably between 7.0 and 8.3. In particular, $HCO_3^-$ ions (also known as bicarbonate) are present in order to adjust the pH into this range of values.

Preferably, at least one bicarbonate salt is present in the composition of the invention. Preferably, the composition according to the invention comprises sodium hydrogen carbonate.

Preferably, the bicarbonate salt is present in the composition according to the invention at a concentration of between 20 and 100 mmol/L, preferably between 20 and 80 mmol/L, more preferably between 20 and 60 mmol/L, even more preferably between 20 and 55 mmol/L.

Preferably, the composition of the invention has an osmolarity of between 250 and 1800 mOsm/L, preferably between 280 and 1600 mOsm/L, more preferably between 280 and 1500 mOsm/L.

The composition according to the invention comprises at least one saccharide (compound a)). The saccharide improves cell survival and function by maintaining the osmotic balance. A fraction penetrates the cells and stabilizes the membrane structures. The saccharide is preferably selected among the monosaccharides, disaccharides, and trisaccharides.

The monosaccharides are preferably selected among glucose, galactose, fructose, and mannose. Preferably, the saccharide is glucose.

The disaccharide preferably has the formula A-B, where A and B are each independently selected among glucose, fructose, and mannose. The saccharide is preferably a disaccharide. The disaccharide is preferably a dimer of glucose. More preferably, the disaccharide is selected among trehalose and sucrose.

The trisaccharides are preferably selected among raffinose (trimer of galactose, glucose, and fructose), maltotriose, and isomaltotriose (trimers of glucose).

The saccharide is preferably present in the composition according to the invention in a concentration of between 10 and 20 mmol/L, preferably between 10 and 15 mmol/L, more preferably between 12.5 and 15 mmol/L.

The composition according to the invention comprises at least one amino acid (compound b)). Preferably, the amino acid is selected among glutamine, alanyl-glutamine, tryptophan, lysine, methionine, phenylalanine, threonine, valine, leucine and isoleucine, arginine, histidine, tyrosine, cysteine, and mixtures thereof.

More preferably, the amino acid is cysteine; preferably said cysteine is provided as cystine, said cystine being a cysteine dimer.

Preferably the composition according to the invention comprises at least one mixture of glutamine and alanyl-glutamine, in particular a mixture of L-glutamine and L-alanyl-L-glutamine.

Preferably, the composition according to the invention comprises essential amino acids. An essential amino acid is an amino acid that cannot be synthesized de novo by the organism (usually human) or that is synthesized at an insufficient rate, and must therefore be supplied by the diet, a necessary condition for the organism to function properly.

In humans, there are eight essential amino acids: tryptophan, lysine, methionine, phenylalanine, threonine, valine, leucine and isoleucine.

Preferably, the composition according to the invention comprises the eight essential amino acids mentioned above, as well as arginine, histidine, tyrosine, and cysteine. Such a mixture of amino acids is in particular marketed by Thermo Fisher under the reference Gibco® MEM Amino Acids 50X.

The amino acids are preferably present in the composition according to the invention in a concentration of between 10 and 700 mg/L, preferably between 50 and 700 mg/L, more preferably between 100 and 700 mg/L, even more preferably between 150 and 700 mg/L, even more preferably between 200 and 700 mg/L, even more preferably between 250 and 700 mg/L, even more preferably between 300 and 700 mg/L, even more preferably between 300 and 600 mg/L.

The composition according to the invention preferably comprises a mixture of the eight essential amino acids mentioned above, arginine, histidine, tyrosine, cysteine, glutamine, and alanyl-glutamine.

The composition according to the invention preferably comprises at least one vitamin. Preferably, the composition according to the invention comprises at least one vitamin selected among vitamin B1 (thiamine), B2 (riboflavin), B4 (choline), B5 (pantothenic acid), B6 (pyridoxal), B7 (inositol), B9 (folic acid), PP (nicotinamide), and mixtures thereof.

Such a mixture of vitamins is commercially available in particular from Thermo Fisher under the reference Gibco® MEM Vitamin Solution (100×).

The vitamin(s) is (are) preferably present in the composition according to the invention in a concentration of between 0.1 and 100 mg/L, preferably between 0.5 and 90 mg/L, more preferably between 1 and 80 mg/L, even more preferably between 1.5 and 70 mg/L, even more preferably between 2 and 60 mg/L, even more preferably between 2.5 and 50 mg/L, even more preferably between 3 and 40 mg/L, even more preferably between 3.5 and 30 mg/L, even more preferably between 4 and 20 mg/L, even more preferably between 4.5 and 20 mg/L, even more preferably between 5 and 10 mg/L.

The composition according to the invention comprises at least DMSO or at least one C3-C5 alkanediol (compound c)).

DMSO, or dimethylsulfoxide, is an organic polar aprotic solvent of formula CH3-SO—CH3. It is an intracellular cryoprotectant whose main purpose is to replace the intracellular fluid, thus preventing the formation of ice crystals and the osmotic stress inherent in the freeze/thaw phases that can burst the membrane structures.

DMSO is preferably present in the composition according to the invention in an amount between 2 and 20% inclusive by volume relative to the total volume of the composition, preferably between 3 and 15% inclusive by volume relative to the total volume of the composition, more preferably between 5 and 10% inclusive.

The C3-C5 alkanediol is preferably a linear, branched, or cyclic alkane comprising from 3 to 5 carbon atoms and 2 hydroxyl groups. Preferably, it is selected among the linear alkanes comprising from 3 to 5 carbon atoms and 2 hydroxyl groups. More preferably, it is selected among 1,2-propanediol (also called propylene glycol), 1,5-pentanediol, and 2,3-butanediol. The C3-C5 alkanediol is preferably 1,2-propanediol (also called propylene glycol).

The C3-C5 alkanediol is preferably present in the composition according to the invention in an amount between 2 and 20% inclusive by volume relative to the total volume of the composition, preferably between 3 and 15% inclusive by volume relative to the total volume of the composition, more preferably between 5 and 10% inclusive.

The composition according to the invention comprises at least one antioxidant (compound d)). "Antioxidant" is understood to mean any compound which enables slowing or preventing the oxidation caused by an oxidizing agent that can lead to the production of free radicals. In the composition of the present invention, the antioxidant makes it possible to protect cells from oxidative stress and thus to maintain or improve their viability.

Preferably, the composition according to the invention comprises at least one antioxidant selected among glutathione, vitamin C, vitamin E, vitamin A, L-cysteine, or coenzyme Q10.

Preferably, the composition according to the invention comprises glutathione.

Preferably, the antioxidant(s) is (are) present in the composition according to the invention in a concentration of between 0.1 and 2 g/L, preferably between 0.2 and 1.75 g/L, more preferably between 0.3 and 1.5 g/L.

Preferably, the composition according to the invention comprises human albumin.

Preferably, human albumin is present in the composition according to the invention in a concentration of between 0 and 6 g/L, preferably between 1.5 and 5 g/L, more preferably between 2 and 4 g/L.

Preferably, the composition according to the invention comprises a platelet lysate. The platelet lysate is preferably present in the composition according to the invention in a concentration of between 5% and 30% by volume, preferably between 15% and 25% by volume relative to the total volume of the composition.

Preferably, the platelet lysate comprises at least one growth factor selected among TGF-beta1, EGF, PDGF-AB, IGF-1, VEGF, bFGF, and mixtures thereof.

Preferably, the composition according to the invention is substantially free of dextran. "Substantially free" composition is understood to mean that this composition contains less than 10% by weight of dextran, preferably less than 5% by weight, more preferably less than 3% by weight, more preferably less than 1% by weight. Preferably, the composition according to the invention does not contain any dextran.

Preferably, the composition according to the invention comprises, in an aqueous medium comprising electrolytes:
a) glucose,
b) a mixture of glutamine, alanyl-glutamine, tryptophan, lysine, methionine, phenylalanine, threonine, valine, leucine, isoleucine, arginine, histidine, tyrosine, and cysteine,
c) DMSO or at least one C3-C5 alkanediol, preferably in a concentration of between 3% and 15% by volume relative to the total volume of the composition, and
d) glutathione.

The composition according to the invention is of particular interest, and is intended for the cryopreservation of at least one sample of cells for therapeutic purposes. Indeed, the compounds a) to d) used in the composition make it possible to cryopreserve the cells for therapeutic purposes in a lasting and effective manner.

"Cryopreservation" is understood to mean that: the viability of cells maintained at a temperature between 4° C. and 20° C. for 1 hour after thawing, said thawing following a step of freezing at a temperature between −150 and −180° C. inclusive, is between 90% and 100%; the viability of cells maintained at a temperature between 4° C. and 20° C. for 3 hours after thawing, said thawing following a step of freezing at a temperature between −150 and −180° C. inclusive, is between 80% and 100%; and the viability of cells maintained at a temperature between 4° C. and 20° C. for 4 hours after thawing, said thawing following a step of freezing at a temperature between −150 and −180° C. inclusive, is between 60% and 100%.

In one embodiment of the invention, cell viability is directly measured on the cells in the composition of the invention by flow cytometry after staining the cells with 7-aminoactinomycin D (7-AAD) which is a marker of cell viability. In a second embodiment, cell viability is directly measured on the cells in the composition of the invention by counting with a cell counter such as Nucleocounter after staining with Acridine Orange (cell marker) and DAPI (cell death marker).

"Cells for therapeutic purposes" is understood to mean cells which in themselves constitute the therapeutic product and which are administered to the patient. These cells are distinct from cells that are cultured for the production of biological drugs, for example such as CHO, HEK, or YB2/0 cells.

Among the cells for therapeutic purposes, particular mention may be made of advanced therapy drugs or cell therapy products.

The cells for therapeutic purposes (compound e)) are preferably selected among:
immune cells, such as NK cells, monocytes, B cells, natural or genetically modified T cells, such as regulatory T cells, tumor-infiltrating T cells, cytotoxic T cells, helper T cells, and chimeric antigen receptor (CAR) T cells;
myoblasts, in particular human ones;
hematopoietic stem cells;
mesenchymal stem cells;
cardiac cells;
fibroblasts; and
any other natural or genetically modified cells.

NK cells (or NK lymphocytes) are cells of innate immunity. These are non-T (CD3−) non-B (CD19−) cells, characterized in humans by the markers CD56, CD16, and NK.

Monocytes are leukocytes that evolve into macrophages, dendritic cells, or osteoclasts.

B cells are the immune cells responsible for the production of antibodies.

Regulatory T cells are a subset of CD4+ T cells, which inhibit the proliferation of other effector T cells.

Cytotoxic T cells are a subset of CD8+ T cells that destroy infected cells.

Helper T cells are a subset of CD4+ T cells that mediate the immune response.

Finally, chimeric antigen receptor (CAR) T cells, also called CAR T cells, correspond to a particular technology of cellular engineering. These are T cells that express a chimeric antigen receptor. CAR T cells are able to kill cancer cells by recognizing and binding to the tumor antigen present in said cancer cells.

The sample of cells for therapeutic purposes may come from the patient to be treated (in this case the patient and the donor are the same person), via biopsy or blood sample. In this case, the composition obtained, once cryopreserved and then thawed, will be administered to the same patient: it is an autologous product.

Alternatively, the sample of cells for therapeutic purposes may come from another source (i.e. another individual, cellular engineering), in particular via biopsy or blood sample. In this case, the composition obtained, once cryopreserved and then thawed, will be administered to a patient to be treated who is other than the donor: it is an allogeneic product.

Preferably, the composition according to the invention comprises a cell concentration of between 2 and 300 M cells/mL, preferably between 10 and 200 M cells/mL, more preferably between 50 and 200 M cells/mL.

The present invention also relates to a method for the cryopreservation of at least one sample of cells for therapeutic purposes, comprising the following steps:
 i) mixing the sample of cells for therapeutic purposes with:
  a) at least one saccharide,
  b) at least one amino acid,
  c) DMSO or at least one C3-C5 alkanediol,
  d) at least one antioxidant, and
  a physiologically acceptable medium, so as to obtain a composition having a pH between 7.0 and 8.5, preferably between 7.0 and 8.3, then
 ii) freezing the composition obtained in step i).

In this method, the step of mixing the sample of cells for therapeutic purposes with the various compounds described above is typically done by dilution. The mixing may be done at a temperature between +1° C. and +20° C. inclusive, preferably between +2° C. and +20° C. inclusive, even more preferably between +2° C. and +15° C. inclusive, even more preferably between +2° C. and +10° C. inclusive, even more preferably between +2° C. and +6° C. inclusive, even more preferably at 4° C.

Preferably, the sample of cells for therapeutic purposes is cultured beforehand in vitro in a suitable culture medium. Then it is centrifuged, the supernatant is removed, and the pellet is suspended in a mixture of physiologically acceptable medium and of compounds a) to d) described above, to obtain a composition having a pH between 7.0 and 8.5, preferably between 7.0 and 8.3.

The freezing step (step ii)) is preferably carried out by lowering the temperature from +20° C. to a temperature between −100° C. and −180° C., preferably between −140° C. and −160° C. Preferably, the freezing step (step ii)) is carried out by lowering the temperature from +4° C. to a temperature between −100° C. and −180° C., preferably between −140° C. and −160° C.

The sample is then stored at a temperature below −130° C. in general. Preferably, the freezing ii) is carried out by placing the mixture obtained in step i) in a container immersed in a mixture of isopropyl alcohol at +4° C., then bringing the whole to a temperature between −70° C. and −100° C. or −70° C. and −90° C. or −70° C. and −80° C. Due to the slow cooling of the alcohol, this system ("freezing in Nalgene container") allows an almost linear temperature decrease of between −1° C. and −2° C. per minute. Alternatively and preferably, the freezing ii) is done using a programmable freezer.

Preferably, the freezing ii) is carried out, in particular with the aid of a programmable freezer, by the following steps:
 placing the mixture obtained in step i) at a temperature of +4° C.; then
 decreasing the temperature by 1° C. per minute, from 4° C. to −40° C.; then
 decreasing the temperature by 10° C. per minute, from −40° C. to −180° C., to reach a final storage temperature of about −180° C.

The frozen product thus obtained can be stored for a few months at −180° C. These temperatures are the ones applied to the sample.

The invention is illustrated by the following examples, which are in no way limiting.

EXAMPLE 1: CRYOPRESERVATION OF MYOBLASTS

The myoblasts can be prepared as described in application FR2810045.

Assay 1:

a/Experimental Protocols

Cell Viability:

Measurement of viability by the Nucleocounter NC200 from Chemometec (hereinafter "NC") is carried out via a cell counter: the cells are stained in the presence of Acridine Orange (which stains all the cells) and by DAPI (which stains only dead cells which have a permeabilized membrane). The ratio between the two provides the cell viability.

Myoblast Percentage:

The myoblast percentage is measured by flow cytometry. It corresponds to the percentage of CD56+, CD15− living cells after staining the cells with specific CD56, CD15 antibodies and propidium iodide (PI). Indeed, the product tested also contains impurities which are CD56− and CD15+ or − cells and which can overwhelm the myoblasts because they are less demanding in terms of culture. The goal is to maintain the myoblast percentage in the product after freezing.

The cells are formulated in the cryopreservation solutions tested ("DMSO 5%" and "DMSO 10%"). They are then frozen at −180° C. Their viability is measured immediately after thawing and 3 hours after thawing, on cells maintained at room temperature in the cryopreservation medium tested.

| b/Results: | | |
|---|---|---|
| Volumes in μL | DMSO 5% | DMSO 10% |
| Solution of 5X ions glutathione* | 1000 | 1000 |
| Water | 750 | 500 |
| PlasmaLyte* | 425 | 425 |
| Bicarbonate 1.4 (333 mOsm/L) | 1325 | 1325 |
| Vitamins (Gibco MEM Vitamin Solution (100X)) | 50 | 50 |

-continued b/Results:

| Volumes in µL | DMSO 5% | DMSO 10% |
|---|---|---|
| Amino acids (Gibco MEM Amino Acids 50X) | 100 | 100 |
| Platelet lysate | 1000 | 1000 |
| Glutamax** (100X), liquid | 100 | 100 |
| DMSO | 250 | 500 |
| pH at +4° C. | 7.57 | 7.63 |
| Before freezing | | |
| Viability by NC | 97.3 | |
| % myoblasts by flow cytometry | 64.2 | |
| After freezing and thawing | | |
| Viability by NC at thaw (%) | 93.7 | 92.4 |
| % myoblasts by flow cytometry immediately after thawing | 61.5 | 64.5 |
| Viability by NC at T3 h (%) | 91.5 | 89.4 |

*See below
**200 mM L-alanyl-L-glutamine mixture
*** Composition in platelet lysate These results show that:
- the "DMSO 5%" and "DMSO 10%" formulations are effective for the cryopreservation of myoblasts: the cell viability immediately after thawing is greater than 90% and the cell viability 3 hours after thawing is greater than 85%,
- the cell viability immediately after thawing and 3 hours after thawing is stable, which means that the formulations do not induce delayed cell stress and that the developed formulation can be used clinically without requiring prior washing of the cells,
- the amount of myoblasts before freezing and immediately after thawing is very close (64.2% before freezing, 61.5% after thawing for the "DMSO 5%" solution and 64.5% for the "DMSO 10%" solution). The tested solutions thus make it possible to maintain the percentage of myoblasts in the product.

Assay 2:

a/Experimental Protocols

Cell Viability:

Measurement of viability by the Nucleocounter NC200 from Chemometec (hereinafter "NC") is carried out via a cell counter: the cells are stained with Acridine Orange (cell marker) and DAPI (cell death marker). The ratio between the two provides the cell viability.

Apoptosis:

The apoptosis test makes it possible to determine the early mortality of cells by apoptosis. The principle of the apoptosis test is based on double staining using SYTOX Green (membrane integrity marker—dead cell marker) and Annexin V (early apoptosis marker) analyzed by flow cytometry. This staining makes it possible to distinguish between cells in early apoptosis (SYTOX−/Annexin V+), dead cells (SYTOX+/Annexin V+), and living cells (SYTOX−/Annexin V−).

Myogenic Differentiation Test:

The myogenic differentiation test measures the expression of myosin (which is a contractile protein of myotubes, in other words the differentiated myoblasts). It is a known marker of the differentiation that reflects myoblast functionality. The cells are differentiated in a serum-depleted medium for 4 days, to form myotubes (=elongated cells resulting from the fusion of several myoblasts with contractile capacity), and the percentage of differentiated cells is measured by flow cytometry using a specific antibody. This functional capacity is directly correlated to the effectiveness of the freezing formulations since they must preserve the differentiating capacity of the cells when thawed.

The cells are formulated in the cryopreservation solutions tested. They are then frozen at −180° C. The various tests (viability, apoptosis, phenotype) are then carried out 1 hour after thawing, on cells maintained at room temperature in the cryopreservation media tested.

b/Results

| Volume in µL | Sol 4 | Sol 4bis | Sol 5 | Sol 18 | Sol 22 | Sol 28 | Sol 30 | Sol 32 | Sol 29 | Sol 24bis |
|---|---|---|---|---|---|---|---|---|---|---|
| Solution of 5× ions* | | | | | 2000 | | | | 2000 | |
| Solution of 5× ions + glutathione* | 2000 | 2000 | 2000 | 2000 | | 2000 | | | | |
| Solution of 2.5× ions + glutathione* | | | | | | | | 2000 | | |
| Water for injection | 1250 | 1250 | 1000 | 2160 | 950 | 2250 | | 1250 | 950 | 1960 |
| Ringer's solution* | 850 | 2850 | 850 | 2200 | 1060 | 1850 | | 850 | 1100 | 1890 |
| Ringer's solution + glutathione* | | | | | | | 4100 | | | |
| 1.4% liquid bicarbonate (333 mOsm/L) | 2650 | 2650 | 2650 | 2650 | 2650 | 2650 | 2650 | 2650 | 2650 | 2650 |
| Vitamins (MEM Vitamin Solution 100× from Gibco) | 100 | 100 | 100 | | 100 | 100 | 100 | 100 | 100 | 100 |
| Amino acids (MEM Amino Acid 50× from Gibco) | 200 | 200 | 200 | | | 200 | 200 | 200 | | 200 |
| Platelet lysate*** | 2000 | | 2000 | | 2000 | | 2000 | 2000 | 2000 | 2000 |
| bFGF | | 100 ng | | | | | | | | |
| Liquid Glutamax (100×) ** | 200 | 200 | 200 | 200 | 200 | 200 | 200 | 200 | 200 | 200 |
| DMSO | 750 | 750 | 1000 | 750 | 1000 | 750 | 750 | 750 | 1000 | 1000 |
| L-cysteine (1.2 g + 10 mL water) | | | | 40 | 40 | | | | | |
| Total | 10000 | 10000 | 10000 | 10000 | 10000 | 10000 | 10000 | 10000 | 10000 | 10000 |
| pH T + 24 h at +3 +/−2° C. | 7.57 | 7.43 | 7.60 | 7.38 | 7.60 | 7.39 | 7.96 | 7.75 | 7.73 | 7.97 |

*See below
** 200 mM L-alanyl-L-glutamine mixture
***Composition in platelet lysate

| Myoblasts | Time | Formulation | Viability NC200 | Difference compared to before freezing | Apoptosis % live | Difference compared to before freezing | % of myosin cells + |
|---|---|---|---|---|---|---|---|
| Myoblasts 1 | before freezing | | 98.6 | | 93.4 | | NA |
| | T1 h post thaw | Sol 4 | 96.2 | −2% | 87.3 | −7% | 15.5 |
| | | Sol 28 | 95.5 | −3% | 85.7 | −8% | 15.2 |
| | | Sol 4bis | 94.2 | −4% | 88.8 | −5% | 17.8 |
| | | Sol 18 | 95.1 | −4% | 87.0 | −7% | 16.7 |
| | | Sol 30 | 95.4 | −3% | 84.7 | −9% | 10.3 |
| | | Sol 5 | 97.8 | −1% | 84.6 | −9% | 15.2 |
| | | Sol 32 | 96.4 | −2% | 90.3 | −3% | 8.4 |
| | | Sol 22 | 96.7 | −2% | 87.6 | −6% | 7.0 |
| | | Sol 29 | 98.0 | −1% | 87.0 | −7% | 6.3 |
| | | Sol 24bis | 98.7 | −3% | 72.4 | −23% | 8.7 |
| Myoblasts 2 | before freezing | | 98.0 | | 94.2 | | NA |
| | T1 h post thaw | Sol 4 | 95.7 | −2% | 94.6 | 0% | 28.6 |
| | | Sol 28 | 95.0 | −3% | 90.5 | −4% | 6.0 |
| | | Sol 4bis | 95.1 | −3% | 86.4 | −8% | 17.0 |
| | | Sol 18 | 95.5 | −3% | 91.6 | −3% | 28.8 |
| | | Sol 30 | 95.2 | −3% | 93.0 | −1% | 11.9 |
| | | Sol 5 | 96.0 | −2% | 94.3 | 0% | 13.8 |
| | | Sol 32 | 97.3 | −1% | 92.9 | −1% | 8.4 |
| | | Sol 22 | 96.4 | −2% | 88.3 | −6% | 4.3 |
| | | Sol 29 | 95.2 | −3% | 86.5 | −8% | 7.2 |
| | | Sol 24bis | 96.5 | −2% | 87.6 | −7% | 7.0 |

These results show that:
The formulations tested are effective for the cryopreservation of myoblasts: the cell viability rate 1 hour after thawing is greater than 90%,
The tested formulations make it possible to have a high level of non-apoptotic cells,
The cells remain functional 1 hour after thawing: they express myosin, which means that they retain their ability to differentiate.

EXAMPLE 2: CRYOPRESERVATION OF MESENCHYMAL STEM CELLS (MSC)

The mesenchymal stem cells can be prepared as described in Sensebé L, Bourin P, Tarte K. *Good manufacturing practices production of mesenchymal stem/stromal cells*. Hum Gene Ther. January 2011; 22(1): 19-26.
a/Experimental Protocols
Cell Viability
Measurement of viability by flow cytometry is carried out after staining the cells with 7-aminoactinomycin D (7-AAD) which is a cell viability marker. 7-AAD has a strong DNA binding affinity which living cells effectively block. The dead cells therefore remain stained with 7-AAD, while the living cells are not stained.
Apoptosis:
The apoptosis test makes it possible to determine early mortality of cells by apoptosis. The principle of the apoptosis test is based on double staining using SYTOX green (membrane integrity marker—dead cell marker) and Annexin V (early apoptosis marker), analyzed by flow cytometry. This staining makes it possible to distinguish between cells in early apoptosis (SYTOX−/Annexin V+), dead cells (SYTOX+/Annexin V+), and living cells (SYTOX−/Annexin V−).
Phenotype:
An analysis of cell phenotype is performed to determine the stability of the MSC formulation in solutions 4 and 5. The phenotype is analyzed by flow cytometry and corresponds to the percentage of CD90+/CD73+/CD45−/CD34− cells using specific CD90, CD73, CD45, and CD34 antibodies conjugated to a fluorochrome.

"HA4%" corresponds to the reference solution in which the cells are formulated solely in 4% human albumin and stored for 24 hours at +3±2° C.

Drug Substance "DS" corresponds to the cells resulting from the harvest at the end of the process, before formulation.

The cells are formulated in the cryopreservation solutions tested. They are then frozen at −180° C. The various tests (viability, apoptosis, phenotype) are then carried out 4 hours and 6 hours after thawing, maintained at room temperature in the cryopreservation media tested.

| b/Results | | |
|---|---|---|
| Volume in μL | Sol 4 | Sol 5 |
| Solution of 5X ions + glutathione* | 2000 | 2000 |
| Water for injection | 1250 | 1000 |
| Ringer's solution* | 850 | 850 |
| 1.4% liquid bicarbonate (333 mOsm/L) | 2650 | 2650 |
| Vitamins (MEM Vitamin Solution 100X from Gibco) | 100 | 100 |
| Amino acids (MEM Amino Acid 50X from Gibco) | 200 | 200 |
| Platelet lysate *** | 2000 | 2000 |
| Liquid Glutamax (100X) ** | 200 | 200 |
| DMSO | 750 | 1000 |
| Total | 10000 | 10000 |
| pH | 7.57 | 7.60 |

*See below
** 200 mM L-alanyl-L-glutamine mixture
*** Composition in platelet lysate

Cell viability

| Lot | State | Time | Formulation | 7AAD | % difference compared to DP 24 h |
|---|---|---|---|---|---|
| MSC 1 | DS | T0 | DS | 94.5 | |
| | HA4% | T24 h | HA4% | 53.72 | |
| | frozen | T4 h | Sol 4 | 63.7 | 18.6% |
| | frozen | T6 h | | 65.3 | 21.6% |
| | frozen | T4 h | Sol 5 | 60.8 | 13.2% |
| | frozen | T6 h | | 52.4 | −2.5% |
| MSC 2 | DS | T0 | DS | 93.5 | |
| | HA4% | T24 h | HA4% | 48.6 | |
| | frozen | T4 h | Sol 4 | 62.2 | 28.0% |
| | frozen | T6 h | | 56.3 | 15.8% |
| MSC 3 | DS | T0 | DS | 95.2 | |
| | HA4% | T24 h | HA4% | 61.6 | |
| | frozen | T4 h | Sol 4 | 83.7 | 35.9% |
| | frozen | T6 h | | 75 | 21.8% |
| | frozen | T4 h | Sol 5 | 70.5 | 14.4% |
| | frozen | T6 h | | 62.3 | 1.1% |

Apoptosis

| Lot | State | Time | Formulation | % cells not apoptotic | % difference compared to DP 24 h |
|---|---|---|---|---|---|
| MSC 1 | DS | T0 | DS | 89.1 | |
| | HA4% | T24 h | HA4% | 19.8 | |
| | frozen | T4 h | Sol 4 | 58.6 | 196% |
| | frozen | T6 h | | 55.2 | 179% |
| | frozen | T4 h | Sol 5 | 52 | 163% |
| | frozen | T6 h | | 56.4 | 185% |
| MSC 2 | DS | T0 | DS | 79.8 | |
| | HA4% | T24 h | HA4% | 26 | |
| | frozen | T4 h | Sol 4 | 42.01 | 62% |
| | frozen | T6 h | | 59.9 | 130% |
| MSC 3 | DS | T0 | DS | 89.7 | |
| | HA4% | T24 h | HA4% | 49.8 | |
| | frozen | T4 h | Sol 4 | 70.6 | 42% |
| | frozen | T6 h | | 67.4 | 35% |
| | frozen | T4 h | Sol 5 | 89.3 | 79% |
| | frozen | T6 h | | 78.4 | 57% |

Phenotype

| Lot | State | Time | Formulation | CD90 Spec ≥ 95% | CD73 Spec ≥ 95% | CD45 Spec ≤ 5% | CD34 Spec ≤ 2% |
|---|---|---|---|---|---|---|---|
| MSC 1 | DS | T0 | DS | 99.3 | 99.1 | 0.3 | 0.3 |
| | HA4% | T24 h | HA4% | 97.9 | 97.1 | 0.2 | 0.4 |
| | frozen | T4 h | Sol 4 | 99.6 | 97.4 | 0.1 | 0.1 |
| | frozen | T6 h | | 99.6 | 99 | 0.1 | 0.1 |
| | frozen | T4 h | Sol 5 | 99.6 | 96.3 | 0.1 | 0.2 |
| | frozen | T6 h | | 99.5 | 98.5 | 0.1 | 0.2 |
| MSC 2 | DS | T0 | DS | 99.4 | 99.5 | 0.5 | 0.9 |
| | HA4% | T24 h | HA4% | 99.7 | 90 | 0.1 | 0.3 |
| | frozen | T4 h | Sol 4 | 99.8 | 99.6 | 0 | 0.2 |
| | frozen | T6 h | | 99.4 | 99.4 | 0.1 | 0.2 |
| MSC 3 | DS | T0 | DS | 99.8 | 99.7 | 0.1 | 0.2 |
| | HA4% | T24 h | HA4% | 99.5 | 99.1 | 0.3 | 0.2 |
| | frozen | T4 h | Sol 4 | 99.4 | 82.2 | 0.4 | 0.5 |
| | frozen | T6 h | | 99.5 | 99.9 | 0.1 | 0.4 |
| | frozen | T4 h | Sol 5 | 99.3 | 98 | 0.1 | 0.4 |
| | frozen | T6 h | | NA | 99.9 | 0.2 | 0.6 |

The results show:

The tested formulations 4 and 5 are effective for the cryopreservation of MSCs: the cell viability rate 4 hours after thawing is greater than 60%, the level of non-apoptotic cells is greater than the reference solution and is high (greater than 85%), the phenotype of the MSCs formulated in solutions 4 and 5 is well preserved 4 or 6 hours after thawing (more than 80% of the cells express CD90 and CD73 markers, less than 1% of the cells express CD45 and CD34 markers).

The ingredient "Solution of 5× ions" corresponds to:

| Solution of 5X ions (per 20 mL of solution) | |
|---|---|
| PlasmaLyte (see below) | 20 mL |
| Magnesium | 32.5 mg |
| Glucose | 270.3 mg |
| Sodium acetate | 172.3 mg |
| Trisodium citrate | 276.5 mg |
| Citric acid | 92.2 mg |

The ingredient "Solution of 5× ions glutathione" corresponds to:

| Solution of 5X ions glutathione (per 20 mL of solution) | |
|---|---|
| PlasmaLyte (see below) | 20 mL |
| Magnesium | 32.5 mg |
| Glucose | 270.3 mg |
| Sodium acetate | 172.3 mg |
| Trisodium citrate | 276.5 mg |
| Citric acid | 92.2 mg |
| Reduced glutathione | 33.8 mg |

The ingredient "Solution of 5× ions 50% water" corresponds to:

| Solution of 5X ions 50% water (per 20 mL of solution) | |
|---|---|
| Water for injection (WFI) | 10 mL |
| PlasmaLyte (see below) | 10 mL |

-continued

| | Solution of 5X ions 50% water (per 20 mL of solution) |
|---|---|
| Magnesium | 32.5 mg |
| Glucose | 270.3 mg |
| Sodium acetate | 172.3 mg |
| Citric acid | 276.5 mg |
| Reduced glutathione | 92.2 mg |

The ingredient "Solution of 5× ions 50% water+glutathione" corresponds to:

| | Solution of 5X ions 50% water + glutathione (per 20 mL of solution) |
|---|---|
| Water for injection (WFI) | 10 mL |
| PlasmaLyte (see below) | 10 mL |
| Magnesium | 32.5 mg |
| Glucose | 270.3 mg |
| Sodium acetate | 172.3 mg |
| Trisodium citrate | 276.5 mg |
| Citric acid | 92.2 mg |
| Reduced glutathione | 33.8 mg |

The ingredient "Solution of 5× ions Ringer's solution+glutathione" corresponds to:

| | Solution of 5X ions Ringer's solution + glutathione (per 20 mL of solution) |
|---|---|
| Ringer's solution (see below) | 20 mL |
| Magnesium | 32.5 mg |
| Glucose | 270.3 mg |
| Sodium acetate | 172.3 mg |
| Trisodium citrate | 276.5 mg |
| Citric acid | 92.2 mg |
| Reduced glutathione | 33.8 mg |

The "Solution of 2.5× ions+glutathione" corresponds to:

| | Solution of 2.5X ions + glutathione per 20 mL of solution |
|---|---|
| Ringer's | 20 mL |
| Magnesium | 16.3 |
| Glucose | 135.2 |
| Sodium acetate | 86.1 |
| Trisodium citrate | 138.2 |
| Citric acid | 46.1 |
| Reduced glutathione | 16.9 |

The "PlasmaLyte" ingredient corresponds to:

| | PlasmaLyte (per 1000 mL of solution) |
|---|---|
| NaCl | 5.26 g |
| KCl | 0.37 g |
| MgCl2 | 0.30 g |
| Sodium acetate trihydrate (C2H3NaO2) | 3.68 g |
| Sodium gluconate | 5.02 g |
| Water for injection (WFI) | q.s. ad. 1000 mL |

The "Ringer's Solution" ingredient corresponds to:

| | Ringer's solution (per 1000 mL of solution) |
|---|---|
| NaCl | 8.60 g |
| KCl | 0.30 g |
| Calcium chloride dihydrate | 0.33 g |
| Water for injection (WFI) | q.s. ad. 1000 mL |

***Composition of the Platelet Lysate

| Growth factor | concentration in pg/mL | Relative standard deviation (%) |
|---|---|---|
| PDGF-AB | 60000 | 8.39 |
| IGF-1 | 49000 | 3.88 |
| EGF | 3500 | 4.79 |
| VEGF | 910 | 4.22 |
| bFGF | 150 | 6.33 |

The invention claimed is:

1. A composition comprising, in a physiologically acceptable medium:
   a) at least one saccharide,
   b) at least one amino acid,
   c) DMSO or at least one C3-C5 alkanediol,
   d) at least one antioxidant,
   e) platelet lysate, and
   f) cells for therapeutic purposes,
   said composition having a pH between 7.0 and 8.5,
   wherein the cells for therapeutic purposes are natural or genetically modified T cells or myoblasts.

2. The composition according to claim 1, wherein its pH is between 7.0 and 8.3.

3. The composition according to claim 1, wherein the saccharide is a monosaccharide, disaccharide, or trisaccharide.

4. The composition according to claim 1, wherein the amino acid is selected from glutamine, alanyl-glutamine, tryptophan, lysine, methionine, phenylalanine, threonine, valine, leucine and isoleucine, arginine, histidine, tyrosine, cysteine, and mixtures thereof.

5. The composition according to claim 1, wherein the amino acid is cysteine.

6. The composition according to claim 1, wherein the cysteine is in the form of cystine, said cystine being a cysteine dimer.

7. The composition according to claim 1, further comprising at least one vitamin.

8. The composition according to claim 1, wherein the vitamin is selected from vitamins B1, B2, B4, B5, B6, B7, B9, PP, and mixtures thereof.

9. The composition according to claim 1, wherein the C3-C5 alkanediol is selected from the linear alkanes comprising from 3 to 5 carbon atoms and 2 hydroxyl groups.

10. The composition according to claim 1, wherein the C3-C5 alkanediol is propylene glycol.

11. The composition according to claim 1, wherein the antioxidant is glutathione, vitamin C, vitamin E, vitamin A, L-cysteine, or coenzyme Q10.

12. The composition according to claim 1, wherein the antioxidant is glutathione.

13. The composition according to claim 1, further comprising human albumin.

14. The composition according to claim 1, further comprising at least one bicarbonate salt.

15. The composition according to claim 1, wherein myoblasts are human ones.

16. The composition according to claim 1, wherein the physiologically acceptable medium is an aqueous medium comprising electrolytes, and wherein the composition comprises:
  a) glucose,
  b) a mixture of glutamine, alanyl-glutamine, tryptophan, lysine, methionine, phenylalanine, threonine, valine, leucine, isoleucine, arginine, histidine, tyrosine, and cysteine,
  c) DMSO or at least one C3-C5 alkanediol,
  d) glutathione, and
  e) cells for therapeutic purposes.

17. A method for the cryopreservation of at least one sample of cells for therapeutic purposes, comprising:
  i) mixing the sample of cells for therapeutic purposes with:
    a) at least one saccharide,
    b) at least one amino acid,
    c) DMSO or at least one C3-C5 alkanediol,
    d) at least one antioxidant,
    e) platelet lysate, and
    a physiologically acceptable medium, to obtain a composition having a pH between 7.0 and 8.5, wherein said cells are natural or genetically modified T cells or myoblasts, and
  ii) freezing the composition obtained in step i).

18. The method according to claim 17, wherein the pH is between 7.0 and 8.3.

19. The method according to claim 17, wherein the freezing ii) is carried out to a temperature between −100° C. and −180° C.

20. The method according to claim 17, wherein the freezing step ii) is carried out by placing the composition obtained in step i) in a container immersed in a mixture of isopropyl alcohol at +4° C., then bringing the whole to a temperature between −70° C. and −100° C.

21. A method for the cryopreservation of at least one sample of cells for therapeutic purposes, said method comprising mixing said sample of cells with a composition comprising, in a physiologically acceptable medium:
  a) at least one saccharide,
  b) at least one amino acid,
  c) DMSO or at least one C3-C5 alkanediol,
  d) at least one antioxidant,
  e) platelet lysate, and having a pH between 7.0 and 8.5, wherein said cells are natural or genetically modified T cells or myoblasts.

22. The cryopreservation method according to claim 21, wherein the composition has a pH between 7.0 and 8.3.

* * * * *